(12) United States Patent
Hamed et al.

(10) Patent No.: US 7,074,301 B2
(45) Date of Patent: Jul. 11, 2006

(54) CHEMICALLY CROSS-LINKED CELLULOSE FIBER AND METHOD OF MAKING SAME

(75) Inventors: Othman A. Hamed, Jesup, GA (US); Harry J. Chmielewski, Brunswick, GA (US); Dana B. McBee, Jesup, GA (US)

(73) Assignee: Rayonier Products and Financial Services Company, Jesup, GA (US)

( * ) Notice: Subject to any disclaimer, the term of this patent is extended or adjusted under 35 U.S.C. 154(b) by 243 days.

(21) Appl. No.: 10/166,254

(22) Filed: Jun. 11, 2002

(65) Prior Publication Data

US 2003/0230391 A1 Dec. 18, 2003

(51) Int. Cl.
- D21H 11/20 (2006.01)
- D21H 17/47 (2006.01)
- D21H 21/22 (2006.01)
- D06M 15/39 (2006.01)

(52) U.S. Cl. ............ 162/157.6; 162/72; 162/158; 162/168.1; 162/165; 8/116.1; 8/116.4

(58) Field of Classification Search ............ 162/9, 162/72, 90, 91, 95, 141, 146–149, 135–137, 162/158, 164.1, 165–167, 157.6, 168.1, 183, 162/100, 109, 111, 188; 8/116.1, 116.4; 604/374–376, 378, 358, 367, 372; 264/121, 264/128; 424/402

See application file for complete search history.

(56) References Cited

U.S. PATENT DOCUMENTS

| | | | |
|---|---|---|---|
| 2,764,573 A | 9/1956 | Reibnitz et al. |
| 3,112,156 A | 11/1963 | Vail et al. |
| 3,224,926 A | 12/1965 | Bernardin |
| 3,241,553 A | 3/1966 | Steiger |
| 3,260,565 A | 7/1966 | Beachem |
| 3,434,918 A | 3/1969 | Bernardin |
| 3,756,913 A | 9/1973 | Wodka |
| 3,932,209 A | 1/1976 | Chatterjee |
| 4,035,147 A | 7/1977 | Sangenis et al. |
| 4,204,054 A | 5/1980 | Lesas et al. |
| 4,472,167 A | 9/1984 | Welch |
| 4,820,307 A | 4/1989 | Welch et al. |
| 4,882,453 A | 11/1989 | Chelsea |
| 4,889,595 A | 12/1989 | Herron et al. |
| 4,936,865 A | 6/1990 | Welch et al. |
| 5,042,086 A | 8/1991 | Cole et al. |
| 5,137,537 A | 8/1992 | Herron et al. |
| 5,225,047 A | 7/1993 | Graef et al. |

(Continued)

FOREIGN PATENT DOCUMENTS

EP 0427316 7/1997

(Continued)

*Primary Examiner*—Eric Hug
(74) *Attorney, Agent, or Firm*—Hunton & Williams LLP

(57) ABSTRACT

The present invention relates to cross-linked cellulosic fiber having improved absorbency characteristics when compared to conventional cross-linked fibers. The cross-linked cellulosic fiber is obtainable by reacting pulp in the sheet or fluff form with one or more reagents selected from organic molecule having acid and aldehyde functional groups "acid aldehydes." The invention also relates to a method of producing the cross-linked fiber. The method includes heating the treated cellulosic fibers to promote intrafiber cross-linking. The cross-linked fibers are characterized by having an improved centrifuge retention capacity, fluid acquisition rate, resiliency, absorbent capacity, absorbency under load, and other absorbent properties. The inventive cross-linked fibers are useful in forming absorbent composites, and in particular absorbent cores for use in absorbent articles.

31 Claims, 7 Drawing Sheets

U.S. PATENT DOCUMENTS

| | | | |
|---|---|---|---|
| 5,273,549 A | 12/1993 | Didier et al. | |
| 5,399,240 A | 3/1995 | Graef et al. | |
| 5,547,541 A * | 8/1996 | Hansen et al. | 162/12 |
| 5,858,021 A * | 1/1999 | Sun et al. | 162/90 |
| 5,938,995 A * | 8/1999 | Koltisko et al. | 264/128 |
| 6,063,982 A * | 5/2000 | Martin et al. | 604/374 |
| 6,162,541 A * | 12/2000 | Chou et al. | 428/376 |
| 6,207,278 B1 | 3/2001 | Jewell et al. | |
| 6,290,867 B1 | 9/2001 | Kielbania, Jr. et al. | |
| 6,620,293 B1 * | 9/2003 | Sears et al. | 162/157.6 |
| 6,821,383 B1 * | 11/2004 | Shore et al. | 162/9 |
| 2002/0096279 A1 * | 7/2002 | Leithman et al. | 162/90 |
| 2005/0142965 A1 * | 6/2005 | LaFortune | 442/59 |

FOREIGN PATENT DOCUMENTS

| | | | |
|---|---|---|---|
| WO | 97/04162 | * | 2/1997 |
| WO | 9931312 | | 6/1999 |

* cited by examiner

CHEMICALLY CROSS-LINKED CELLULOSE FIBER AND METHOD OF MAKING SAME

FIELD OF THE INVENTION

The present invention relates to cross-linked cellulosic fiber, obtainable by reacting pulp in sheet or fluff form with one or more reagents selected from organic molecules having acid and aldehyde groups (e.g., acid aldehydes). The invention also relates to a method of producing the cross-linked fiber. The cross-linked fibers of the present invention are characterized by having an improved acquisition rate, softness, resiliency, absorbent capacity, centrifuge retention capacity, free swell, and absorbency under load.

DESCRIPTION OF RELATED ART

Absorbent articles intended for personal care, such as adult incontinent pads, feminine care products, and infant diapers typically are comprised of at least a top sheet, a back sheet, an absorbent core disposed between the top sheet and back sheet, and an acquisition layer between the top sheet and the absorbent core. The acquisition layer comprised of, for example, acquisition fibers, usually is incorporated in the absorbent articles to provide better distribution of liquid, increase the rate of liquid absorption, and reduce gel blocking. A wide variety of acquisition fibers are known in the art. Included among these are synthetic fibers, a composite of cellulosic fibers and synthetic fibers, and cross-linked cellulosic fiber. Cross-linked cellulose fiber is preferred because it is abundant, it is biodegradable, and it is relatively inexpensive.

Cross-linked cellulose fibers and processes of making them have been described in the literature for many years (see, for example G. C. Tesoro, Cross-Linking of Cellulose, in *Handbook of Fiber Science and technology*, Vol II, M. Lewis and S. B. Sello eds. pp 1–46, Mercel Decker, New York (1993)). The cross-linked cellulose fibers typically are made by reacting cellulose with multifunctional agents that are capable of reacting with the hydroxyl groups of the anhydroglucose repeating units of the cellulose either in the same chain, or in neighboring chains simultaneously. Cross-linked cellulose fibers generally are characterized by their high absorbent capacity, and their high resiliency in the wet and dry states.

Many cross-linking agents have been discovered since the development of cross-linked cellulose fibers. Formaldehyde and urea-formaldehyde products were among the first agents used to cross-link cellulosic fibers. Such cross-linking agents are disclosed in, for example, U.S. Pat. Nos. 2,764, 573; 3,260,565; 3,112,156; 3,224,926; 3,241,553; 3,932, 209; 3,756,913; 4,035,147; and 5,225,047, the disclosures of which are incorporated by reference herein in their entirety.

Safety problems have arisen from the use of formaldehyde and urea-formaldehyde products as cross-linking agents. These problems have created a need for non-formaldehyde-containing cross-linking agents to replace the formaldehyde and urea-formaldehyde cross-linking agents. A number of new cross-linking agents for cellulosic fibers have become available in light of this need.

Monomers having multifunctional groups, such as carboxylic acid groups and aldehyde groups have been widely used as cross-linking agents for cellulosic fibers. For example, alkanepolycarboxylic acids are capable of cross-linking cellulose fibers by forming an ester bond with the fiber's hydroxyl groups. Cross-linking can occur upon heating the alkanepolycarboxylic acid with the cellulosic fiber in the presence of a catalyst, such as sodium hypophosphite, at a temperature over 165° C. (see for example, U.S. Pat. Nos. 5,273,549; 5,137,537; 4,820,307; 4,936,865; and 5,042,986 and European patent 0,427,316 B1, the disclosures of which are incorporated by reference herein in their entirety). Dialdehydes (for example glyoxal) are capable of cross-linking cellulose hydroxyl groups via acetal bonds (see, for example, U.S. Pat. Nos. 4,889,595; 4,472,167; 4,822,453; and 6,207,278 B1, the disclosures of which are incorporated by reference herein in their entirety).

One problem associated with the use of alkanepolycarboxylic acid is that the cellulosic fibers cross-linked thereby tend to lose their cross-linking upon storage, and revert to uncross-linked fibers. Consequently, the fibers lose their favorable mechanical properties that were obtained upon cross-linking. One attempt to solve this problem was to use polymeric cross-linking agents. World Patent No. WO99/31312 describes the use of a polymeric polycarboxylic acid having a molecular weight of more than 500 as a cross-linking agent for cellulosic fiber. U.S. Pat. No. 6,290,867 B1, the disclosure of which is incorporated by reference herein in its entirety, describes the use of polyhydroxyalkylurea having at least two-urea moieties as a cross-linking agent for cellulosic fibers. Although fiber cross-linking with polymeric polycarboxylic acid has been successful and imparts several advantages to cross-linked fiber, those skilled in the art have sought simple reagents and processes to produce cross-linked cellulosic fibers with reduced discoloration, knots, and knits.

Cellulosic fibers typically are cross-linked in the fluff form. Processes for making cross-linked fiber in the fluff form comprise dipping swollen or non-swollen fiber in an aqueous solution of cross-linking agent, catalyst, and softener. The fiber so treated then usually is cross-linked by heating it at elevated temperatures in the swollen state as described in U.S. Pat. No. 3,241,553, or in the collapsed state after fluffing as described in U.S. Pat. No. 3,224,926, and European patent No. 0,427,316B1 the disclosures of each of which are incorporated by reference herein in their entirety.

Cross-linking of fibers in the fluff form is believed to improve physical and chemical properties of fibers in many ways, such as improving the resiliency (in the dry and wet state), increasing the absorbency, reducing wrinkling, and improving shrinkage resistance. Unfortunately, it has been found that such cross-linking, if carried out on a fiber in the sheet form, tends to create substantial problems in the final product. These problems include severe fiber breakage and increased amounts of knots and nits (hard fiber clumps). These disadvantages render the cross-linked product completely unsuitable for many applications. Several approaches have been tried to overcome these problems, many of which have made the cross-linking even more complicated, time consuming, and costly (see, for example, U.S. Pat. Nos. 5,399,240; 4,204,054; and 3,434,918, the disclosures of which are incorporated by reference herein in their entirety).

The description herein of certain advantages and disadvantages of known cross-linked cellulosic fibers, and methods of their preparation, is not intended to limit the scope of the present invention. Indeed, the present invention may include some or all of the methods and chemical reagents described above without suffering from the same disadvantages.

SUMMARY OF THE INVENTION

In view of the problems associated with some of the known cross-linking processes, there is a need to develop a catalyst-free cross-linking agent that offers the cellulosic fiber with advantages that are seen now with conventional cross-linked fibers made using catalysts. There also is a need to provide a simple, relatively inexpensive process for cross-linking cellulosic fibers in sheet and fluff form that produces cross-linked cellulosic fibers that are substantially free of knots and nits. It will be appreciated, however, that knots are advantageous for some applications, and accordingly, the present invention is not in any way limited to producing cross-linked cellulosic fibers substantially free of knots. The present invention desires to fulfill these needs and provide further related advantages.

It therefore is a feature of an embodiment of the invention to provide cross-linked cellulosic fibers that have improved acquisition rates, softness, resiliency, absorbent capacity, centrifuge retention capacity, free swell, and absorbency under load. It also is a feature of an embodiment of the invention to provide a method of cross-linking a cellulosic fiber that is relatively simple and inexpensive.

In accordance with these and other features of embodiments of the invention, there is provided a chemically cross-linked cellulosic fiber that has a centrifuge retention capacity, as determined in accordance with the testing protocol described herein, of less than about 0.48 grams of a 0.9 wt. % saline solution per gram of fiber (hereinafter "g/g"), and less than about 0.60 g/g when the fiber is cross-linked with at least one acid aldehyde cross-linking agent. The chemically cross-linked cellulosic fiber also preferably has desirable properties, such as a free swell of greater than about 10 g/g, an absorbent capacity of greater than about 9.0 g/g, an absorbency under load of greater than about 8.0 g/g, less than about 10% of knots, less than about 6.5% of fines, an acquisition rate upon the third insult of less than about 10.0 seconds, and an ISO brightness of greater than about 80%. These properties may be achieved singly, or in various combinations with one another.

In accordance with an additional feature of an embodiment of the invention, there is provided a method of making a cross-linked cellulosic fiber that includes supplying a cross-linking agent to a sheet of caustic treated cellulosic fibers, drying, and curing the sheet to provide a cross-linked fiber. Another suitable method includes supplying a cross-linking agent to a cellulose fiber in fluff form, drying, fluffing, and curing the fluff fiber to provide a cross-linked fiber.

In accordance with another feature of an embodiment of the invention, there is provided a method of utilizing the chemically cross-linked cellulosic fibers of the present invention in an absorbent core of an absorbent article, and the absorbent core and absorbent articles made thereby. The present invention also provides a method for incorporating the cross-linked fiber and the absorbent core in an absorbent article.

The cross-linked fibers of the present invention preferably have enhanced bulking characteristics, porosity and absorption, may be substantially free of nits and knots, if desired, are substantially free of discoloration, and have enhanced brightness. These and other objects, features, and advantages of the present invention will appear more fully from the following detailed description of the preferred embodiments of the invention, and the attached drawings.

DETAILED DESCRIPTION OF THE PREFERRED EMBODIMENTS

Figure 1:
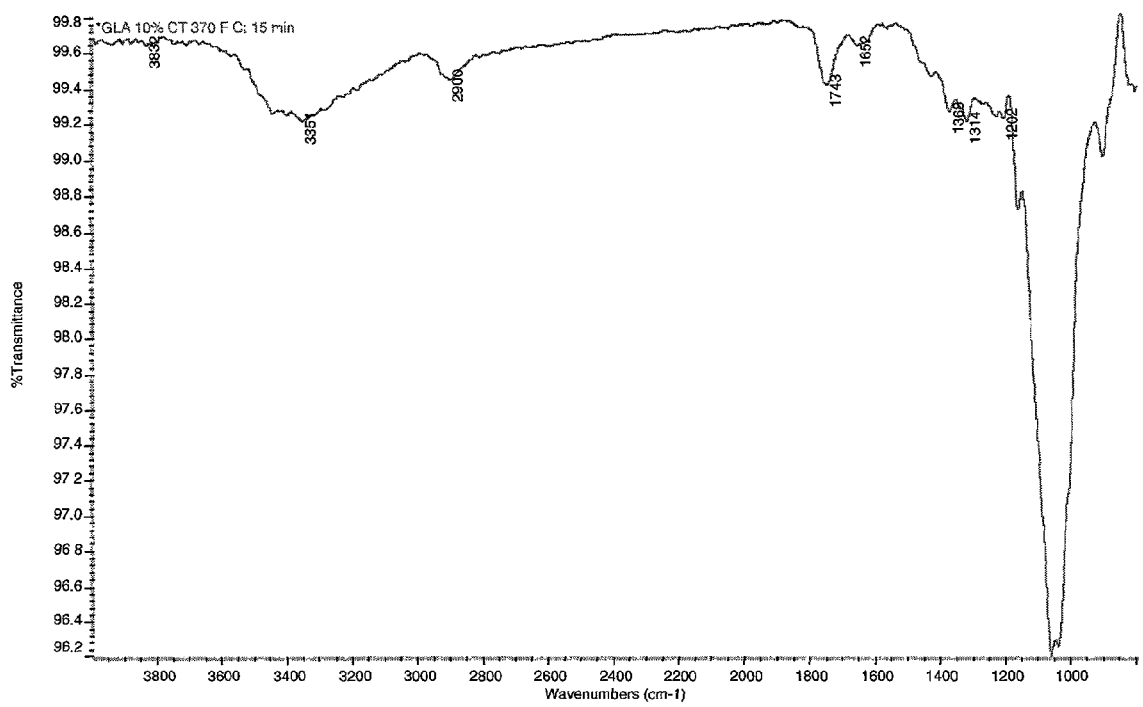
FIG. 1 illustrates an infrared spectrum (IR) of a cross-linked fiber of the present invention, whereby the fiber was treated with 10% glyoxylic acid, dried, and cured at 370° F. for 15 min.

The present invention is directed to chemically cross-linked cellulosic fibers and to a method of making them. The method comprises cross-linking of cellulosic fiber in sheet, roll, or fluff form with a multifunctional cross-linking agent.

As used herein, the terms "absorbent garment," "absorbent article" or simply "article" or "garment" refer to mechanisms that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts.

The present invention may be used with all of the foregoing classes of absorbent garments, without limitation, whether disposable or otherwise. Some of the embodiments described herein provide, as an exemplary structure, a diaper for an infant, however this is not intended to limit the claimed invention. The invention will be understood to encompass, without limitation, all classes and types of absorbent garments, including those described herein.

Throughout this description, the expressions "upper layer," "lower layer," "above" and "below," which refer to the various components included in the absorbent material are used to describe the spatial relationship between the respective components. The upper layer or component "above" the other component need not always remain vertically above the core or component, and the lower layer or component "below" the other component need not always remain vertically below the core or component. Other configurations are contemplated within the context of the present invention.

The term "component" can refer, but is not limited to, designated selected regions, such as edges, corners, sides or the like; structural members, such as elastic strips, absorbent pads, stretchable layers or panels, layers of material, or the like.

Throughout this description, the term "disposed" and the expressions "disposed on," "disposed above," "disposed below," "disposing on," "disposed in," "disposed between" and variations thereof are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent core. It is understood that additional layers may be present between the absorbent core and the top sheet and back sheet, and that additional layers and other materials may be present on the side opposite the absorbent core from either the top sheet or the back sheet.

Throughout this description, the term "impregnated" insofar as it relates to a cross-linking agent impregnated in a fiber, denotes an intimate mixture of cross-linking agents and cellulosic fiber, whereby the cross-linking agent may be adhered to the fibers, adsorbed on the surface of the fibers, or linked via chemical, hydrogen or other bonding (e.g., Van der Waals forces) to the fibers. Impregnated in the context of the present invention does not necessarily mean that the cross-linking agent is physically disposed beneath the surface of the fibers.

Throughout this description, the expression "second" or "secondary cross-linking agent" denotes an additional cross-linking agent, and in no way is intended to mean that the second or secondary cross-linking agent is present in an amount less than the first cross-linking agent. Indeed, a number of embodiments of the invention include those in which the secondary cross-linking agent is present in an amount greater than the first cross-linking agent. For example, a blend of cross-linking agents can be used in the invention whereby the first cross-linking agent is glyoxylic acid and is present in an amount of 20 wt %, and the secondary cross-linking agent is citric acid and is present in an amount of 80 wt %.

The present invention concerns chemically cross-linked fibers that are useful in absorbent articles, and in particular, that are useful in forming absorbent cores or acquisition layers in the absorbent article. The particular construction of the absorbent article is not critical to the present invention, and any absorbent article can benefit from this invention. Suitable absorbent garments are described, for example, in U.S. Pat. Nos. 5,281,207, and 6,068,620, the disclosures of each of which are incorporated by reference herein in their entirety including their respective drawings. Those skilled in the art will be capable of utilizing the chemically cross-linked cellulosic fibers of the present invention in absorbent garments, cores, acquisition layers, and the like, using the guidelines provided herein.

The cellulosic fibers cross-linked in accordance with the present invention, preferably possess characteristics that are desirable in absorbent articles. For example, the cross-linked cellulosic fibers preferably have a centrifuge retention capacity of less than about 0.48 grams of synthetic saline per gram of fiber (hereinafter "g/g"), and less than about 0.60 g/g when cross-linked with an acid aldehyde cross-linking agent. The chemically cross-linked cellulosic fiber also has desirable properties, such as a free swell of greater than about 10 g/g, an absorbent capacity of greater than about 9.0 g/g, an absorbency under load of greater than about 8.0 g/g, less than about 10% of knots, less than about 6.5% of fines, an acquisition rate upon the third insult (or third insult strikethrough) of less than about 10.0 seconds, and an ISO brightness value of greater than about 80%. The particular characteristics of the cross-linked cellulosic fibers of the invention are determined in accordance with the procedures described in more detail in the examples.

The centrifuge retention capacity measures the ability of the fiber to retain fluid against a centrifugal force. It is preferred that the fibers of the invention have a centrifuge retention capacity of less than about 0.48 g/g, when cross-linked with any cross-linking agent, more preferably, less than about 0.45 g/g, even more preferably less than 0.4 g/g, and most preferably less than about 0.39 g/g. The cross-linked cellulosic fibers of the present invention can have a centrifuge retention capacity as low as about 0.37 g/g. It also is preferred that the fibers of the invention have a centrifuge retention capacity of less than about 0.60 g/g, when cross-linked with an acid aldehyde cross-linking agent, more preferably, less than about 0.55 g/g, even more preferably less than 0.5 g/g, and most preferably less than about 0.43 g/g.

The free swell measures the ability of the fiber to absorb fluid without being subjected to a confining or restraining pressure. The free swell preferably is determined by the Teabag method described herein. It is preferred that the fibers of the invention have a free swell of more than about 10 g/g, more preferably, more than about 13 g/g, even more preferably more than 18 g/g, and most preferably more than about 22 g/g. The cross-linked cellulosic fibers of the present invention can have a free swell as high as about 29 g/g.

The absorbent capacity measures the capacity of the fiber to absorb fluid while under a confining or restraining pressure. It is preferred that the fibers of the invention have an absorbent capacity of more than about 9.0 g/g, more preferably, greater than about 9.5 g/g, even more preferably greater than about 10.5 g/g, and most preferably greater than about 11.0 g/g. The cross-linked cellulosic fibers of the present invention can have an absorbent capacity as high as about 16.0 g/g.

The absorbency under load measures the ability of the fiber to absorb fluid against a restraining or confining force over a given period of time. It is preferred that the fibers of the invention have an absorbency under load of greater than about 8.0 g/g, although it can be as low as 7.5 g/g, more preferably, greater than about 8.5 g/g, and most preferably, greater than about 9.0 g/g. The cross-linked cellulosic fibers of the present invention can have an absorbency under load of as high about 14.0 g/g.

The third insult strikethrough measures the ability of the fiber to acquire fluid, and is measured in terms of seconds. It is preferred that the fibers of the invention have a third insult strikethrough of less than about 10.0 seconds, more preferably, less than about 9.7 seconds, even more preferably less than 9.5 seconds, and most preferably less than about 9.0 seconds. The cross-linked cellulosic fibers of the present invention can have a third insult strikethrough of as low as about 6.1 seconds.

The cross-linked fibers of the present invention preferably have less than about 10% of knots, more preferably less than about 5% knots, and most preferably, less than about 3% knots. The cross-linked fibers of the present invention also preferably have less than about 6.5% of fines, preferably less than about 6.3% fines, and most preferably, less than about 6.0% fines. Indeed, the cross-linked cellulosic fibers of the present invention can have fines as low as about 3.2%.

It also is preferred in the present invention, that the cross-linked fibers have a dry bulk of at least about 12 cm$^3$/g fiber, more preferably at least about 12.5 cm$^3$/g fiber, even more preferably at least about 13 cm$^3$/g fiber, and most preferably at least about 13.5 cm$^3$/g fiber.

The ISO brightness measures the brightness of the fibers, and is measured using TAPPI methods T272 and T525. It is preferred that the ISO brightness of the cross-linked fibers of the present invention be greater than 80%, more preferably, greater than about 83%, even more preferably greater than about 84.5%, and most preferably, greater than about 85%. It is preferred that the ISO brightness of the fibers reflect the brightness of the fibers when formed into a pad.

Any cellulosic fibers can be used in the invention, so long as they provide the physical characteristics of the fibers described above. Suitable cellulosic fibers for use in forming the cross-linked fibers of the present invention include those primarily derived from wood pulp. Suitable wood pulp can be obtained from any of the conventional chemical processes, such as the Kraft and sulfite processes. Preferred fibers are those obtained from various soft wood pulp such as Southern pine, White pine, Caribbean pine, Western hemlock, various spruces, (e.g. Sitka Spruce), Douglas fir or mixtures and combinations thereof. Fibers obtained from hardwood pulp sources, such as gum, maple, oak, eucalyptus, poplar, beech, and aspen, or mixtures and combinations thereof also can be used in the present invention. Other cellulosic fiber derived form cotton linter, bagasse, kemp, flax, and grass also may be used in the present invention. The fiber can be comprised of a mixture of two or more of the foregoing cellulose pulp products. Particularly preferred fibers for use in forming the cross-linked fibers of the present invention are those derived from wood pulp prepared by the Kraft and sulfite-pulping processes.

The cellulosic fibers can be derived from fibers in any of a variety of forms. For example, one aspect of the present invention contemplates using cellulosic fibers in sheet, roll, or fluff form. In another aspect of the invention, the fiber can be in a mat of non-woven material. Fibers in mat form are not necessarily rolled up in a roll form, and typically have a density lower than fibers in the sheet form. In yet another feature of an embodiment of the invention, the fiber can be used in the wet or dry state. It is preferred in the present invention that the cellulosic fibers be employed in the dry state.

The fibers of the present invention preferably have a high surface purity of cellulose, but it is not necessarily required that the cellulosic fibers have a high cellulose bulk purity. It is preferred that the cellulosic fiber be cross-linked in the sheet or roll form, and more preferably, be a caustic treated fiber with "high cellulose purity." The high cellulose purity refers to the surface purity of the cellulosic fibers. Throughout this description, the expression "high cellulose purity" refers to pulp comprising at least about 65%, preferably at least 75%, and most preferably, at least about 90% α-cellulose.

The cellulosic fiber that is cross-linked in accordance with the present invention while in the fluff form can be any of wood pulp fibers or fiber from any other source described previously. In another aspect of the invention, the cross-linked fibers in the fluff form suitable for use in the present invention include caustic treated fiber.

Caustic treatment can be carried out by any method known in the art, such as those described in *Cellulose and Cellulose Derivatives*, Vol. V, Part 1, Ott, Spurlin, and Grafllin, eds., Interscience Publisher (1954). Caustic treatment of pulp can be carried out by mixing pulp in an aqueous solution of alkali metal, such as sodium hydroxide, washing, neutralizing or washing and neutralizing, and optionally drying the pulp.

The caustics used in the caustic treatment serve to extract residuals such as lignin and hemicellulose that may be left on the pulp after the pulping and bleaching processes. While not intending on being bound by any theory, the inventors believe that these residuals may be responsible for knots, nits and discoloration in cross-linked fiber prepared by traditional cross-linking methods. In addition, treatment with caustic solution at specific concentrations is capable of converting cellulose from its native structure form, cellulose I, to a more thermodynamically stable and less crystalline form cellulose II.

Reagents suitable for caustic treatment include, but are not limited to, alkali metal hydroxides, such as sodium hydroxide, potassium hydroxide, calcium hydroxide, and rubidium hydroxide, lithium hydroxides, and benzyltrimethylammonium hydroxides. Sodium hydroxyide is a particularly preferred reagent for use in the caustic treatment to produce cellulosic fibers suitable for cross-linking in accordance with the present invention. The pulp of the invention preferably is treated with an aqueous solution containing from about 4 to about 30% by weight sodium hydroxide, more preferably from about 6 to about 20%, and most preferably from about 12 to about 16% by weight, based on the weight of the solution. Caustic treatment may be performed during or after bleaching, purification, and drying. Preferably, the caustic treatment is carried out during the bleaching and/or drying process.

It is preferred in the present invention that the caustic treatment be carried out at or about room temperature. Those skilled in the art will be capable of treating the fibers with caustic at a suitable temperature to effect efficient cross-linking, using the guidelines provided herein.

After caustic extraction, the cellulose fiber can be of any purity, and preferably is of high cellulose purity, containing more than 65% by weight, preferably more than 70%, and even more preferably at least about 80% by weight of α-cellulose. It is even more preferred that the cellulose fiber be comprised of at least about 90% by weight, more preferably at least about 95% by weight, and most preferably at least about 97% by weight of α-cellulose.

Commercially available caustic extractive pulp suitable for use in the present invention include, for example, Porosanier-J-HP, available from Rayonier Performance Fibers Division (Jesup, Ga.), and Buckeye's HPZ products, available from Buckeye Technologies (Perry, Fla.).

Cross-linking agents suitable for use in the present invention include acid aldehydes. As used herein, the term "acid aldehyde" refers to organic molecules having carboxylic acid and aldehyde functional groups, such as glyoxylic acid and succinic semialdehyde. Glyoxylic acid is particularly preferred for use in the present invention.

In accordance with another feature of the invention, the invention provides chemically cross-linked fibers that are cross-linked with a blend of one or more cross-linking agents that include an acid aldehyde and an additional, or second, cross-linking agent. For this embodiment, any cross-linking agent can be used as the secondary cross-linking agent, or additional one or more cross-linking agents. Suitable additional cross-linking agents for use in the present invention include polyepoxides that contain hydrophobic saturated, unsaturated, branched and unbranched alkyls, such as 1,4-cyclohexanedimethanol diglycidyl ether, diglycidyl 1,2-cyclohexanedicrboxylate, N,N-diglycidylaniline, N,N-diglcidyl-4-glycidyloxyaniline, and diglycidyl 1,2,3,4-tetrahydrophthalate and glycerol propoxylate triglycidyl ether. Various combinations of these cross-linking agents also may be used.

Other suitable additional cross-linking agents include $C_2$-$C_9$ polycarboxylic acids, such as butantetracarbocylic acid, citric acid, itaconic acid, maleic acid, tartaric acid, and glutaric acid. Other preferred additional cross-linking agents include polycarbocxylic acids commercially available as, for example, polyacrylic acid, polymaleic acid, polyitaconic acid, polyaspartic acid, and polymethacrylic acid. Particularly preferred combinations of cross-linking agents include a blend of glyoxylic acid and citric acid, a blend of glyoxylic acid and polymaleic acid, and blends of glyoxylic acid, citric acid, and polymaleic acid.

In one feature of an embodiment of the invention, the cross-linking agent may be applied to the cellulose fiber in an aqueous solution. Preferably, the aqueous solution has a pH of from about 1 to about 5, more preferably from about 2 to about 3. The present inventors have discovered that an aqueous solution of an acid aldehyde cross-linking agent can be used as is without any adjacent or additional pH control agent.

In another feature of an embodiment of the invention, a water insoluble additional cross-linking agent, e.g., polyepoxide, may be used. When such a water insoluble additional cross-linking agent is used, it is preferred to add a minor amount of a surfactant (e.g., a few drops—less than 1% by weight), and the cross-linking agents then may be applied to the fiber as a dispersion as opposed to an aqueous solution.

In general any type of surfactant capable of forming a dispersion with the water insoluble additional cross-linking agent can be used. Suitable surfactants include nonionic, anionic, or cationic surfactants, or mixtures and combinations of surfactants that are compatible with each other. Preferably, the surfactant is selected from Triton X-100 (Rohm and Haas), Triton X405 (Rohm and Haas), sodium lauryl sulfate, lauryl bromoethyl ammonium chloride, ethoxylated nonylphenols, polyoxyethylene alky ethers, polyoxyethylene alkyl ethers, and polyoxyethylene fatty acid ester.

The cellulosic fiber preferably is treated with an effective amount of cross-linking agent to achieve the absorbent properties and physical characteristics described herein. Generally, the fibers are treated with from about 1.0% to 10.0% by weight cross-linking agent, more preferably from about 2% to 6%, and most preferably from about 3% to 5%. The additional cross-linking agent, if used, preferably is present in the mixture in the amount of from about 5 to about 90% by weight, based on the total weight of the mixture of cross-linking agents, more preferably, the additional cross-linking agent is present in amount of about 20 to 60% by weight, based on the total weight of the mixture of cross-linking agents.

Optionally, the method of forming the cellulosic fiber in accordance with the invention includes a catalyst to speed up the formation of an ester linkage between the hydroxyl groups of the cellulose and the cross-linking agent acid aldehyde groups. The cross-linking reaction of the present invention, however, does not require a catalyst. To the extent that a catalyst is used, any catalyst known in the art that is capable of accelerating the formation of an ester bond between hydroxyl groups and acid groups could be used in the present invention. Catalysts suitable for cross-linking include alkali metal salts of phosphorous containing acids, such as alkali metal hypophosphites, alkali metal phosphates, alkali metal polyphosphonates, alkali metal phosphates, and alkali metal sulfonates. A particularly preferred catalyst is sodium hypophosphite. A suitable weight ratio of catalyst to acid aldehyde is, for example, from 1:1 to 1:10, preferably 1:2 to 1:6.

A catalyst also may be used to promote the reaction between polyepoxides and cellulose hydroxyl groups, to the extent a cross-linking agent containing polyepoxide groups is used as an additional cross-linking agent. When caustic treated fiber is used as the cellulosic fiber, however, a catalyst is not required. Any catalyst known in the art to accelerate the formation of an ether bond or linkage between the hydroxyl groups of cellulose and an epoxide group can be used in the present invention. Preferably, the catalyst is a Lewis acid selected from aluminum sulfate, magnesium sulfate, and any Lewis acid that contains at least a metal and a halogen, including, for example $FeCl_3$, $AlCl_3$, and $MgCl_2$. The catalyst can be applied to the fiber as a mixture with the cross-linking agent(s), before the addition of the cross-linking agent(s), or after the addition of cross-linking agent(s) to cellulosic fiber.

Any method of applying the cross-linking agent(s) to the fiber can be used in carrying out the cross-linking method of the invention. Acceptable methods include, for example, spraying, dipping, impregnation, and the like. Preferably, the fiber is impregnated with an aqueous solution of cross-linking agent. Impregnation usually creates a uniform distribution of cross-linking agent on the fiber and provides for better penetration of cross-linking agent into the interior part of the fiber.

In one embodiment of the invention, a sheet of caustic treated fiber in the roll form is conveyed through a treatment zone where a cross-linking agent(s) is applied on both surfaces by conventional methods, such as spraying, rolling, dipping, knife coating, or other manners of impregnation. Preferred means of applying the aqueous solution of cross-linking agent(s) to fiber in the roll form is by puddle press, size press, and blade coater.

Fibers in fluff, roll, or sheet form after treatment with the cross-linking agent(s) then are preferably dried and cured in a two stage process, and even more preferably, dried and cured in one stage. Such drying and curing is believed to remove water from the fiber, thereupon inducing the formation of an ester and an ether linkage between the hydroxyl groups of the fiber and the cross-linking agent(s), or "curing." Curing usually is carried out in a forced draft oven preferably from about 300° F. to about 435° F., and more preferably from about 320° F. to about 425° F., and most preferably from about 360° F. to about 390° F. Curing preferably is carried out for a period of time that permits complete fiber drying and efficient cross-linking. It is preferred that the cellulosic fiber be cured for a period of time ranging from about 1 minute to about 25 minutes, and more preferably from about 2 minutes to about 15 minutes, most preferably from about 3 minutes to about 8 minutes.

In the case where the fibers are cross-linked in fluff form, they preferably are defiberized by passing them through a hammermill or the like, and then heated at elevated temperatures to promote cross-linking. The cellulosic fibers in fiber form can be dried at ambient temperatures or at temperatures below the curing temperature. Preferably, the cellulosic fibers in fluff form are treated initially with the cross-linking agent(s), then fluffed, and then dried and cured at elevated temperatures in one procedure.

Where the cellulosic fibers to be treated with the cross-linking agent(s) are in roll or sheet form, it is preferred that the fibers be dried and then cured, and more preferably dried and cured in one procedure. In one feature of an embodiment of the present invention, the fiber in sheet or roll form after having been treated with a solution of cross-linking agent(s) is transported by a conveying device, such as belt or a series of driven rollers, through a two-zone oven for drying and curing. In another feature of an embodiment of the present invention, fibers in the non-woven-mat form after having been treated with a solution of cross-linking agent(s) preferably are transported by a conveying device, such as belt or a series of driven rollers, though a hammermill. The defiberized pulp produced by the hammermill then preferably is conveyed through a two-zone oven for drying and curing, preferably through a one step procedure in a one-zone oven for drying and curing.

The present inventors have surprisingly found that fibers cross-linked in accordance with the present invention with a mixture of cross-linking agent(s), where the secondary or additional cross-linking agent is a polyepoxide, displayed significant increases in absorbency under load, softness, absorbent capacity, free swell, bulk, and brightness.

There are several advantages in the present invention for cross-linking fibers in the sheet form besides being more economical. Fibers cross-linking in sheet form are expected to increase the potential for inter-fiber cross-linking which leads to "knots" and "nits" resulting in poor performance in some applications. For instance, when a standard purity fluff pulp, Rayfloc-J, is cross-linked in sheet form, the "knot" content increases substantially indicating increased deleterious inter-fiber bonding. Examination of these "knots" recovered by classification showed they contained true "nits" (hard fiber bundles). Surprisingly, it was found that high purity mercerized pulp cross-linked in sheet or roll form actually yields far fewer knots and nits than control pulps having conventional cellulose purity. Significantly, fibers in the sheet or roll from that were cross-linked in accordance to the present invention were found to contain far fewer knots than a commercial individualized cross-linked fiber, like those produced by the Weyerhaeuser Company commonly referred to as HBA (for high-bulk additive) and by Proctor & Gamble ("P&G"). It is preferred in the present invention that the cross-linked fibers have less than about 5% knots and nits, more preferably, less than about 4.5%, and most preferably less than about 4%.

Another benefit of using caustic treated cellulose pulp to produce cross-linked pulp in fluff or sheet form according to the present invention is that the color forming bodies (hemicelluloses and lignins) are substantially removed, and the fiber is more stable to color reversion at elevated temperature. Since cross-linking of cellulose requires high temperatures (typically around 185° C. for 10–15 minutes), this can lead to substantial discoloration with the conventional fluff pulps that are presently used. In product applications where pulp brightness is an issue, the use of high purity cellulose pulp according to the present invention offers additional advantages.

Another benefit of the present invention is that cross-linked cellulose pulp sheets made in accordance with the present invention enjoy the same or better performance characteristics as conventional individualized cross-linked cellulose fibers, but avoid the processing problems associated with dusty individualized cross-linked fibers.

Cross-linked cellulosic fibers prepared in accordance with the present invention can be utilized, for example, as a bulking material, in the manufacture of high bulk specialty fiber applications that require good absorbency and porosity. The cross-linked fibers can be used, for example, in non-woven, fluff absorbent applications. The fibers can be used independently, or preferably incorporated into other cellulosic fibers to form blends using conventional techniques, such as air laying techniques. In an airlaid process, the fibers, alone or combined in blends with other fibers are blown onto a forming screen or drawn onto the screen via a vacuum. Wet laid processes may also be used, combining the cross-linked fibers of the invention with other cellulosic fibers to form sheets or webs of blends.

The cross-linked fiber of the present invention can be incorporated into various absorbent articles preferably intended for body waste management such as adult incontinent pads, feminine care products, and infant diapers. The cross-linked fiber can be used as an acquisition layer in the absorbent articles. Also it can be utilized in the absorbent core of the absorbent articles. Towels and wipes also may be made with the cross-linked fibers of the present invention, and other absorbent products such as filters. Accordingly, an additional feature of the present invention is to provide an absorbent core and an absorbent article that includes the chemically cross-linked fibers of the present invention.

The cross-linked fibers of the invention were incorporated into an acquisition layer of an absorbent article, and the absorbent article was tested by the Specific Absorption Rate Test (SART) test method, where acquisition time of the fiber is important. The SART test method is described in detail in the Examples. It was observed that the absorbent article that contained cross-linked fibers of the present invention provided results comparable to those obtained from using commercial cross-linked fiber, especially those cross-linked with citric acid or other polycarboxylic acids. The present inventors unexpectedly discovered that Porosanier-J-HP cross-linked in sheet form in accordance with the present invention provided the best results, as shown by the SART method. Caustic treated fiber cross-linked in fluff form using currently available approaches provided superior acquisition time compared to those derived from conventional purity pulp used in current industrial practice (see Table 10, example 9 below).

As is known in the art, absorbent cores typically are prepared using fluff pulp to wick the liquid, and an absorbent polymer (oftentimes a superabsorbent polymer (SAP)) to store liquid. As noted previously, the cross-linked fibers of the present invention have high resiliency, high free swell capacity, high absorbent capacity and absorbency under load, and low third insult strikethrough times. Furthermore, the cross-linked fibers of the present invention are highly porous. Accordingly, the cross-linked fibers of the present invention can be used in combination with the SAP to prepare an absorbent composite (or core) having improved porosity, bulk, resiliency, wicking, softness, absorbent capacity, absorbency under load, low third insult strikethrough, low centrifuge retention capacity, and the like. The absorbent composite could be used as an absorbent core of the absorbent articles intended for body waste management.

It is preferred in the present invention that the cross-linked fibers be present in the absorbent composite in an amount ranging from about 10 to about 80% by weight, based on the total weight of the composite. More preferably, the cross-linked fibers are present in an absorbent composite from about 20 to about 60% by weight. A mixture of conventional cellulosic fibers and cross-linked fibers of the present invention along with the SAP also can be used to make the absorbent composite. Preferably, the cross-linked fibers of the present invention are present in the fiber mixture in an amount from about 1 to 70% by weight, based on the total weight of the fiber mixture, and more preferably present in an amount from about 10 to about 40% by weight. Any conventional cellulosic fiber may be used in combination with the cross-linked fibers of the invention. Suitable additional conventional cellulosic fibers include any of the wood fibers mentioned previously, caustic treated fibers, rayon, cotton linters, and mixtures and combinations thereof.

Any suitable SAP can be used, or other absorbent material, to form the absorbent composite, absorbent core, and absorbent article of the present invention. The SAP can be in the form of, for example, fiber, flakes, or granules, and preferably is capable of absorbing several times its weight of saline (0.9% solution of NaCl in water) and/or blood. The SAP also preferably is capable of retaining the liquid when it is subjected to a load. Non-limiting examples of superabsorbent polymers applicable for use in the present invention include any SAP presently available on the market, including, but not limited to, polyacrylate polymers, starch graft copolymers, cellulose graft copolymers, and cross-linked carboxymethylcellulose derivatives, and mixtures and combinations thereof.

An absorbent composite made in accordance with the present invention preferably contains the SAP in an amount of from about 20 to about 60% by weight, based on the total weight of the composite, and more preferably from about 30 to about 60% by weight. The absorbent polymer may be distributed throughout an absorbent composite within the voids in the cross-linked fiber or the mixture of cross-linked fibers and cellulosic fibers. In another embodiment, the superabsorbent polymer is attached to the fiber via a binding agent that includes, for example, a material capable of cross-linking the SAP to the fiber via hydrogen bonding, (see, for example, U.S. Pat. No. 5,614,570, the disclosure of which is incorporated by reference herein in its entirety).

A method of making an absorbent composite of the present invention may include forming a pad of cross-linked fibers or a mixture cross-linked fibers and cellulosic fibers, and incorporating particles of superabsorbent polymer in the pad. The pad can be wet laid or airlaid. Preferably the pad is airlaid. It also is preferred that the SAP and cross-linked fibers, or a mixture of cross-linked fibers and cellulosic fibers, are air laid together.

Absorbent cores containing cross-linked fibers and superabsorbent polymer preferably have dry densities of between about 0.1 g/cm$^3$ and 0.50 g/cm$^3$, and more preferably from about 0.2/cm$^3$ to 0.4 g/cm$^3$. The absorbent core can be incorporated into a variety of absorbent articles, preferably those articles intended for body waste management, such as diapers, training pants, adult incontinence products, feminine care products, and toweling (wet and dry wipes).

While not intending on being limited by any theory of operation, the reaction scheme shown below represents one of the possible mechanisms of the fiber reaction with a glyoxylic acid cross-linking agent. The scheme is provided for the purpose of illustrating, not limiting, the cross-linking reaction of the present invention.

As shown in the following scheme, the cross-linking reaction between the cellulosic fiber and glyoxylic acid is a self-catalyzed reaction, which starts at room temperature via the formation of a hemiacetal linkage. The formation of the hemiacetal is promoted by the intra- and inter-hydrogen bonding in the glyoxylic acid molecule (see the reaction scheme below). The hydrogen bonding increases the electrophilicity of the aldehyde carbon and makes it more susceptible to attack by the cellulose hydroxyl groups. As a result, the hemiacetal linkage forms at room temperature. The formation of the hemiacetal linkage is believed to stabilize the glyoxylic acid from decomposing upon heating at high temperature to complete the cross-linking.

In one embodiment, the cross-linked fiber and method of the present invention differs from conventional cross-linking methods whereby the cross-linking of the present invention begins at room temperature. In another embodiment, the cross-linking does not need a catalyst to proceed, and hence, can be considered a "self catalyzed process." In another embodiment, the cross-linking agent is attached to the cellulosic fiber from three sites via a combination of ether and an ester bonding. In another embodiment, after curing the cellulosic fiber is totally free from cross-linking agents, because the non-reacted cross-linking agent decomposes during the curing process.

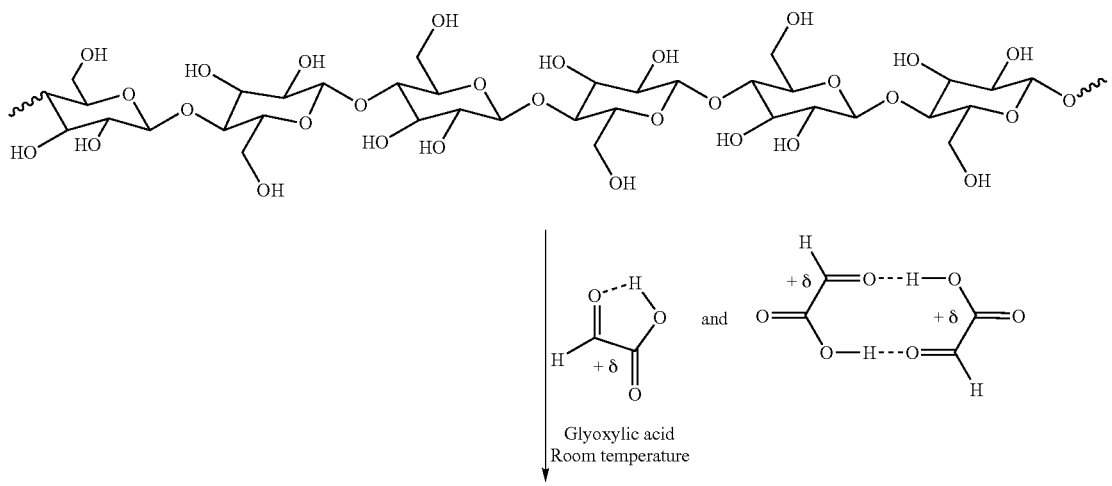

Glyoxylic acid
Room temperature

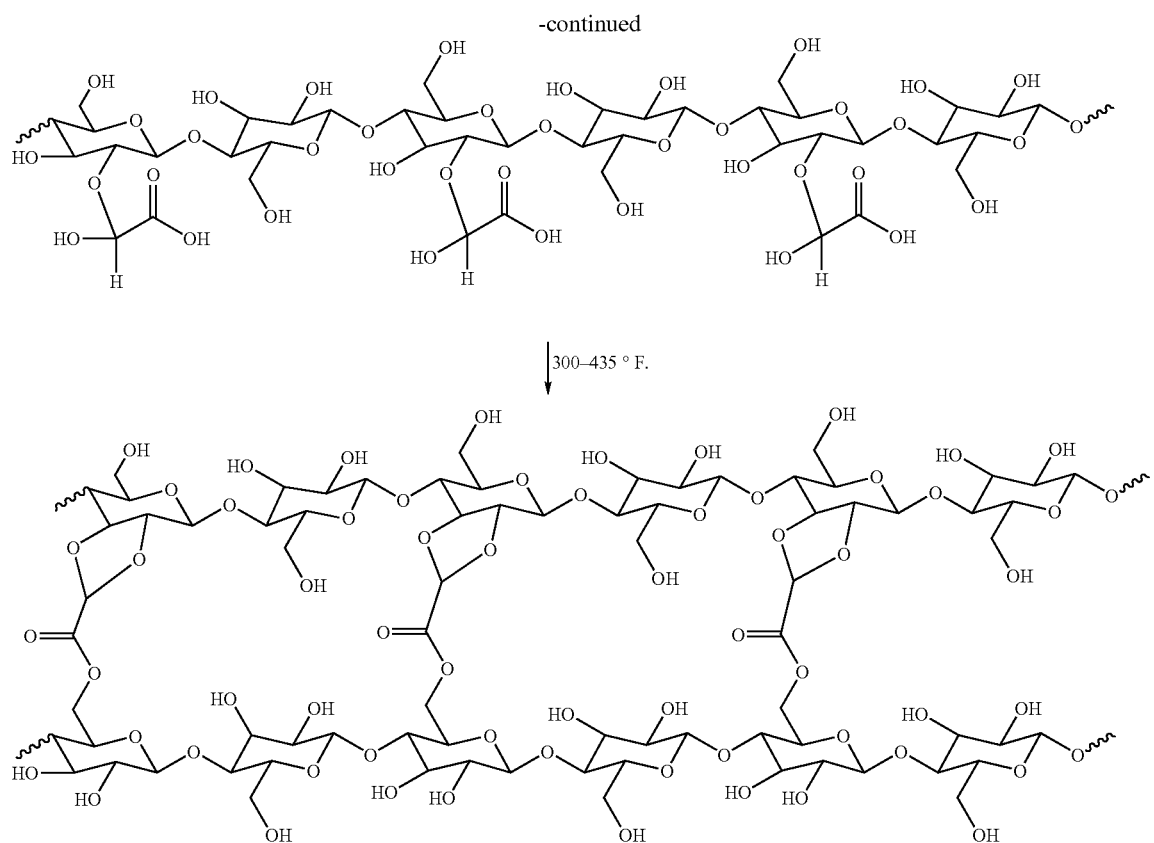

The stability of the cross-links formed in cellulosic fiber of the present invention was examined by an aging process described below in example 8. The cross-linked fiber of the invention showed little or no change in bulk after heating it for about 20 h at 90° C. In addition, fiber stored at ambient temperature and humidity for over 3 months exhibited a bulk that remained unchanged during this period of time.

Figure 2:
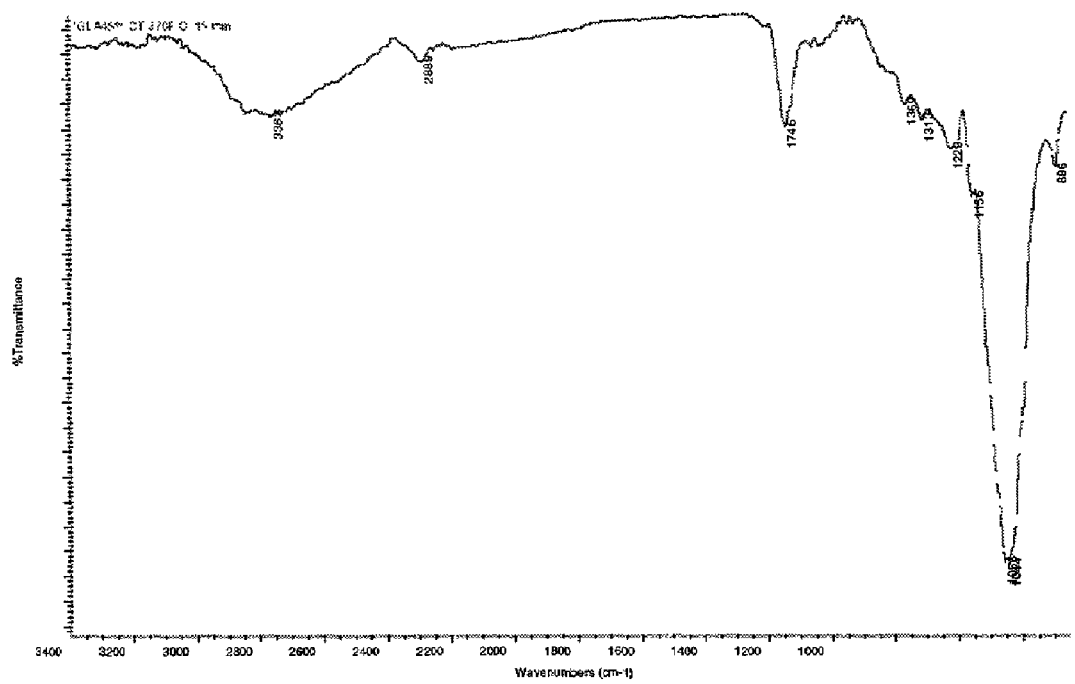
FIG. 2 illustrates an IR of a cross-linked fiber of the present invention, whereby the fiber was treated with 45% glyoxylic acid, dried, and cured at 370° F. for 15 min.

The infrared (IR) spectra of the cross-linked fiber treated in the sheet form with glyoxylic acid are shown in FIGS. 1 and 2. A Nicolet MAGNA 760 FTIR Spectrometer (Madison, Wis., USA) with a Thunderdome was used to collect the infrared spectrum data. IR spectrum shown in FIG. 1 represents a fiber treated with 10% glyoxylic acid dried and cured at 370° F. for 15 min. The IR spectrum shows only one carbonyl-stretching band at 1741 cm$^{-1}$. The band could be assigned to an ester carbonyl stretching. The absence of other carbonyl stretching bands between 1720–1710 cm$^{-1}$ rule out the presence of the carboxyl acid groups. In addition, the absence of the C—H stretching vibration bands typically present in 2830–2695 proves that the aldehyde functional groups are completely reacted.

FIG. 2 illustrates the IR spectrum of a fiber treated with 45% glyoxylic acid, dried and cured at 370° F. for 15 min. The spectrum is similar to that show in FIG. 1. Specifically, the spectrum of FIG. 2 shows the presence of an ester functional group, and the absence of the carboxylic acid and aldehyde functional groups.

Figure 3A:
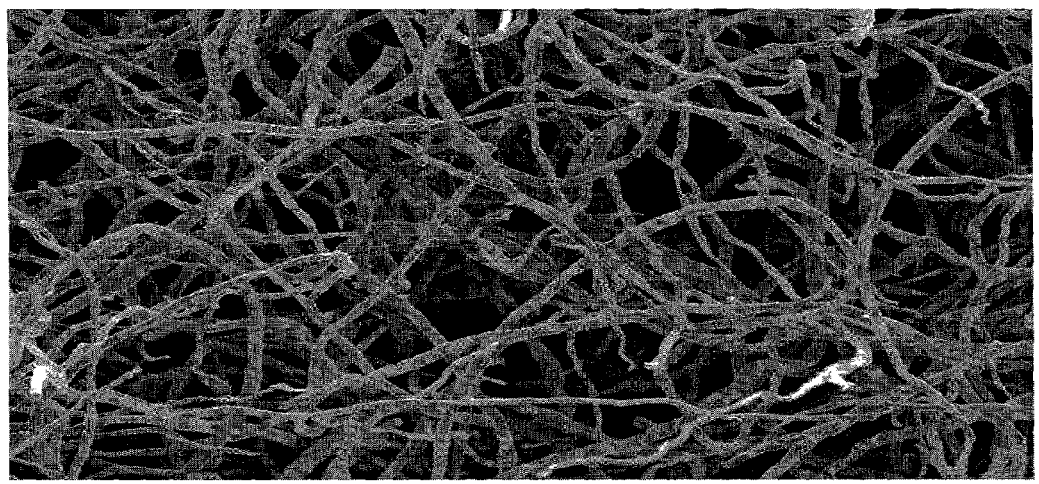
FIGS. 3a and 3b are scanning electron microscope (SEM) photographs of a cross-linked fiber of the present invention.
Figure 3B:
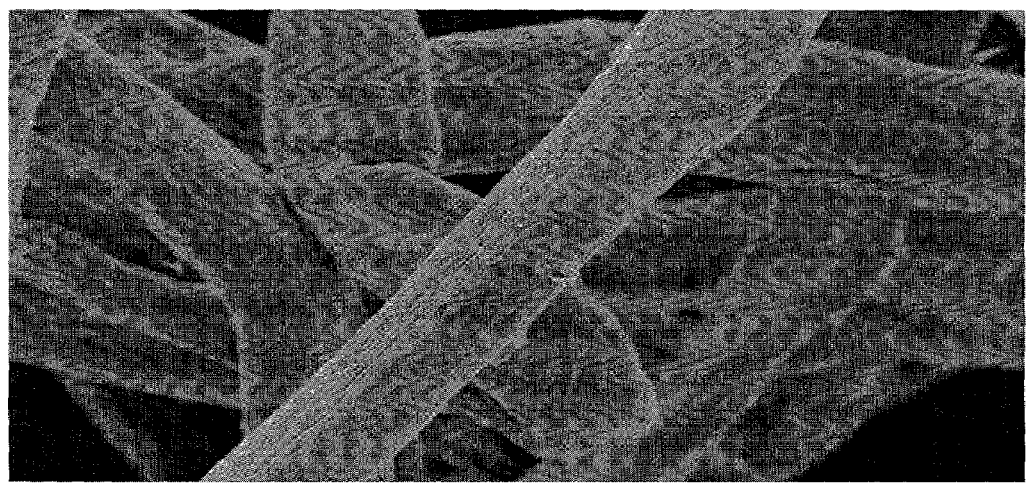

Scanning electron microscope S360 (Leica Cambridge Ltd., Cambridge, England) photographs of representative cross-linked fibers of the present invention obtained from cross-linking of fiber (16%), caustic treated at room temperature, and glyoxylic acid (5%) are illustrated in FIGS. 3A and 3B. The photographs were taken at 75× magnification for FIG. 3A, and 1000× magnification for FIG. 3B.

Figure 4A:
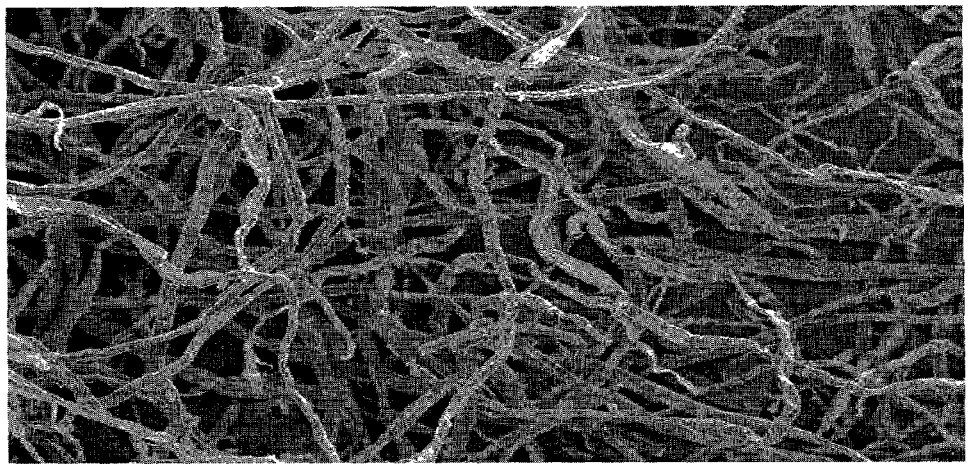
FIGS. 4a and 4b are SEM photographs of a cross-linked fiber of the present invention, taken at different magnifications.
Figure 4B:

Scanning Electron Microscope (SEM) photographs of representative cross-linked fibers of the present invention obtained from cross-linking of conventional fiber (Rayfloc-J) in the fluff form with glyoxylic acid (5%) are shown in FIGS. 4A and 4B. The SEM photographs were taken at 75× magnification for FIG. 4A, and at 350× magnification for FIG. 4B.

Figure 5A:
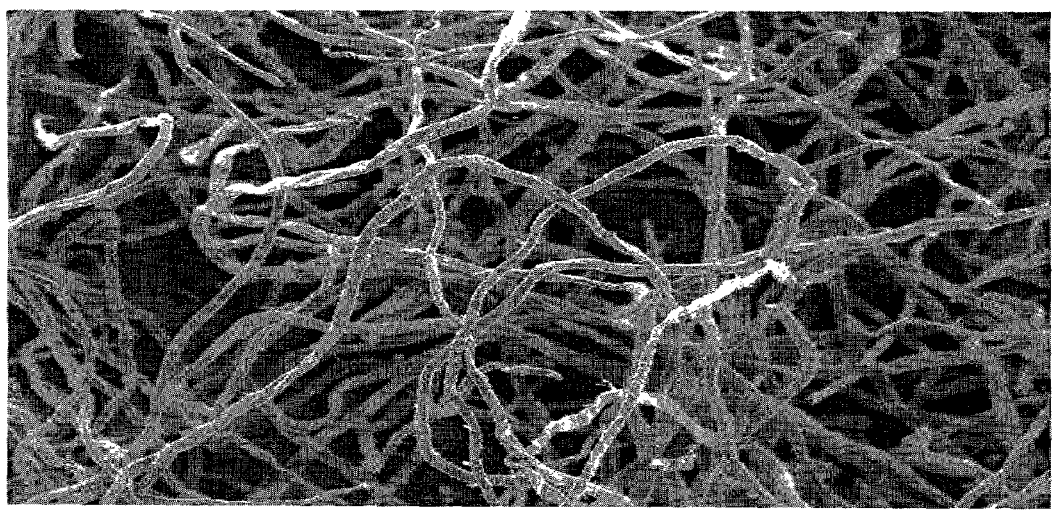
FIGS. 5a and 5b are SEM photographs of a fiber of the present invention cross-linked with a combination of cross-linking agents.
Figure 5B:
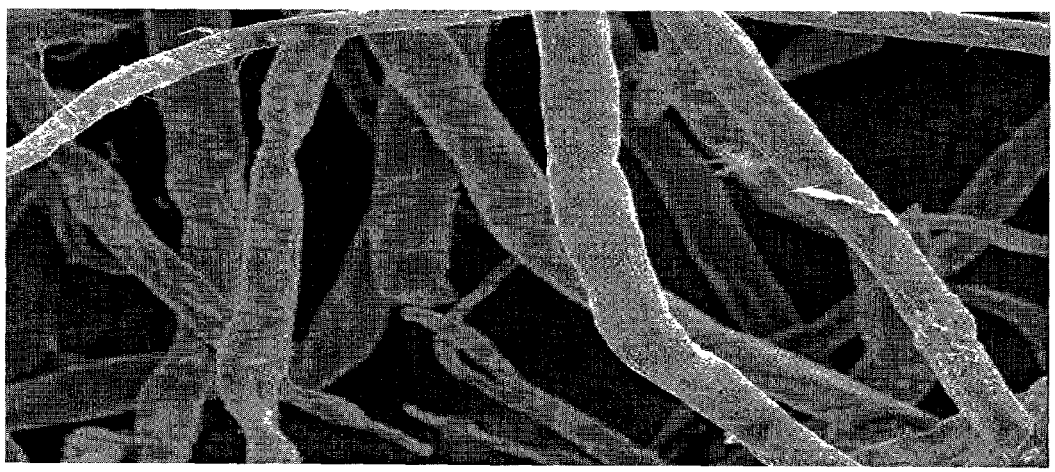

SEM photographs of representative cross-linked fibers of the present invention obtained from cross-linking of fiber (16%) caustic treated at about room temperature with a mixture of glycidyl 1,2-cyclohexane dicarboxylate (1%) and glyoxylic acid (4%) are illustrated in FIGS. 5A and 5B. The SEM photographs were taken at 75× magnification for FIG. 5A, and at 350× magnification for FIG. 5B.

Figure 6A:
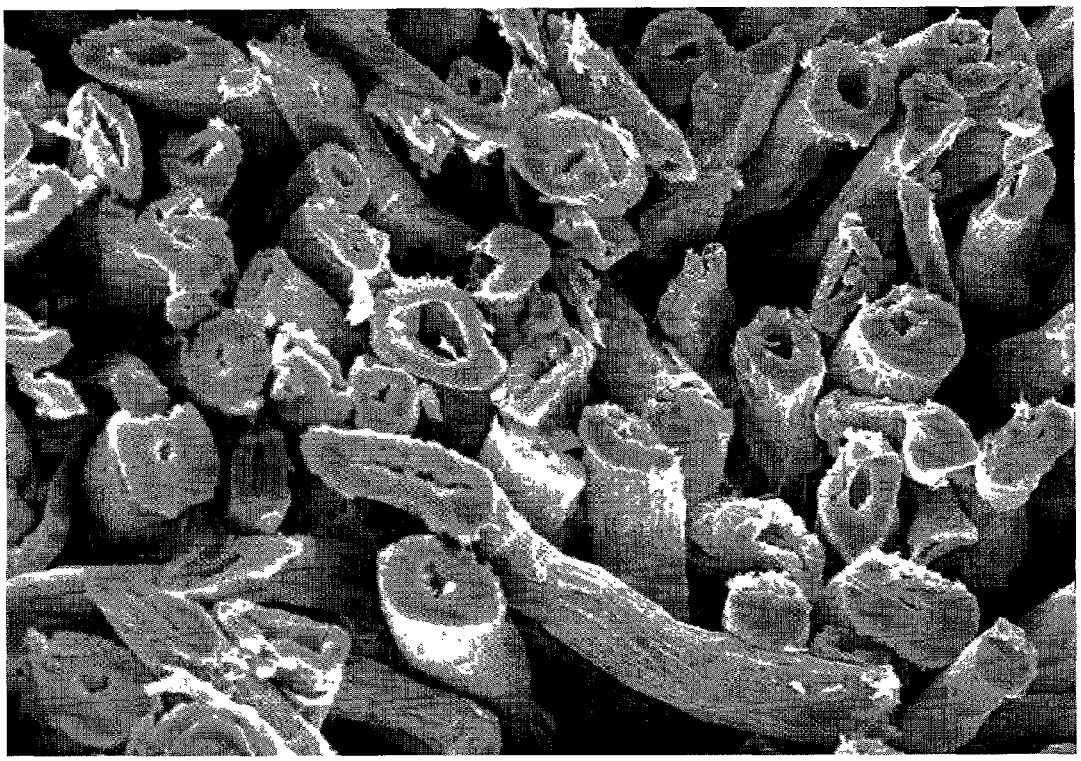
FIGS. 6a and 6b are SEM photographs of cross-sections of a cross-linked fiber of the present invention.
Figure 6B:
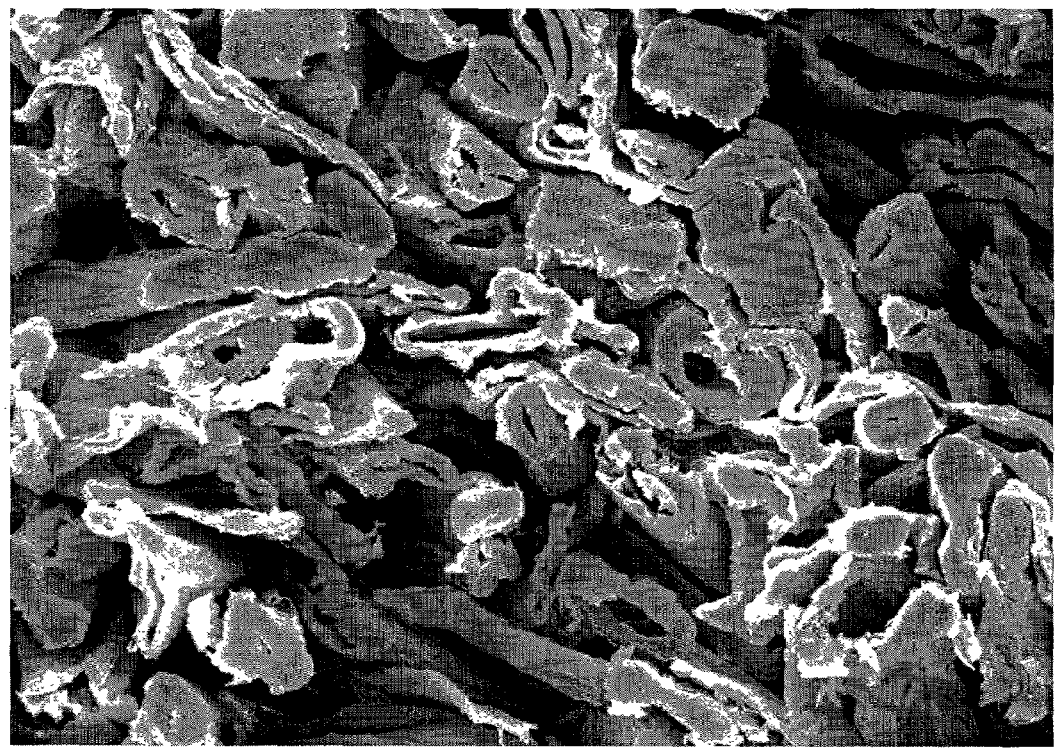

An SEM photograph of the cross section of a representative cross-linked fiber of the present invention obtained from cross-linking fiber (16%) caustic treated at about room temperature with 3% glyoxylic acid is shown in FIG. 6A. The SEM photograph shown in FIG. 6A) was taken at 350× magnification. An SEM photograph of the cross section of a representative cross-linked fiber of the present invention obtained from cross-linking Rayfloc-J fiber with 3% glyoxylic acid is shown in FIG. 6B. The SEM photograph shown in FIG. 6B was taken at 350× magnification.

As shown in these figures, the cross-linked fibers of the present invention are twisted and curled. The cross-linked fibers prepared from caustic treated fiber are round while those prepared from pulp with conventional purity are flat and ribbon-like. Furthermore, the cross-linked fibers of the present invention are highly porous.

To evaluate the various attributes of the present invention, several tests were used to characterize the cross-linked fibers' performance improvements resulting from the presently described method.

The invention will be illustrated but not limited by the following examples.

EXAMPLES

The following test methods were used to measure and determine various physical characteristics of the inventive cross-linked cellulosic fibers.

Test Methods

The Teabag Method

The Teabag Method is a test method used to measure the absorbent capacity under zero load, or "free swell" of the inventive cross-linked fiber. In this test, 2.000 g (±0.001 g) of cross-linked fiber is placed into a pre-weighed (±0.001 g) cloth teabag whereby the open end of the tea bag that contained the cross-linked fiber was sealed with an iron. The teabag and contents then was placed in a pan of 0.9% saline solution and allowed to soak for 30 minutes. The teabag then was removed from the solution, hanged on a drip rack, and allowed to drip dry for 10 minutes. The teabag and contents were weighed and the amount of solution retained in the fibers was determined. A teabag containing no fibers was run under similar conditions, and serves as a blank. The results are used to calculate the amount of saline in grams retained per gram of cross-linked fiber and are expressed as free swell in the units of g/g. The free swell is determined in accordance with the equation below:

Free swell=[Weight of sample−(Weight of dry sample+Weight of teabag+Weight of liquid absorbed by blank)]/Weight of dry sample.

The Absorbency Test Method

The absorbency test method was used to determine the absorbency under load, absorbent capacity, and centrifuge retention capacity of the cross-linked fibers of the present invention. The absorbency test was carried out in a one inch inside diameter plastic cylinder having a 100-mesh metal screen adhering to the cylinder bottom "cell," containing a plastic spacer disk having a 0.995 inch diameter and a weight of about 4.4 g. In this test, the weight of the cell containing the spacer disk was determined to the nearest 0.0001 g, and then the spacer was removed from the cylinder and about 0.35 g of cross-linked fiber having a moisture content within the range of from about 4% to about 8% by weight were air-laid into the cylinder. The spacer disk then was inserted back into the cylinder on the fiber, and the cylinder group was weighed to the nearest 0.0001 g. The fiber in the cell was compressed with a load of 4 psi for 60 seconds, the load then was removed and fiber pad was allowed to equilibrate for 60 seconds. The pad thickness was measured, and the result was used to calculate the dry bulk of the cross-linked fiber.

A load of 0.3 psi then was applied to the fiber pad by placing a 100 g weight on the top of the spacer disk, and the pad was allowed to equilibrate for 60 seconds, after which the pad thickness was measured. The cell and its contents then were hanged in a Petri dish containing a sufficient amount of saline solution (0.9% by weight saline) to touch the bottom of the cell. The cell was allowed to stand in the Petri dish for 10 minutes, and the it was removed and hanged in another empty Petri dish and allowed to drip for 30 seconds. While the pad still was under the load, its thickness was measured. The 100 g weight then was removed and the weight of the cell and contents was determined. The weight of the saline solution absorbed per gram fiber then was determined and expressed as the absorbency under load (g/g).

The absorbent capacity of the cross-linked fiber was determined in the same manner as the test used to determine absorbency under load above, except that this experiment was carried out under a load of 0.01 psi. The results are used to determine the weight of the saline solution absorbed per gram fiber and expressed as the absorbent capacity (g/g).

The cell from the absorbent capacity experiment then was centrifuged for 3 min at 1400 rpm (Centrifuge Model HN, International Equipment Co., Needham HTS, USA), and weighed. The results obtained were used to calculate the weight of saline solution retained per gram fiber, and expressed as the centrifuge retention capacity (g/g).

Fiber Quality

Fiber quality evaluations were carried out on an Op Test Fiber Quality Analyzer (Op Test Equipment Inc., Waterloo, Ontario, Canada) and Fluff Fiberization Measuring Instruments (Model 9010, Johnson Manufacturing, Inc., Appleton, Wis., USA).

Op Test Fiber Quality Analyzer is an optical instrument that has the capability to measure average fiber length, kink, curl, and fines content.

Fluff Fiberization Measuring Instrument is used to measure knits and fine contents of fiber. In this instrument, a sample of fiber in fluff form was continuously dispersed in an air stream. During dispersion, loose fibers passed through a 16 mesh screen (1.18 mm) and then through a 42 mesh (0.36 mm) screen. Pulp bundles (knots) which remained in the dispersion chamber and those that were trapped on the 42-mesh screen were removed and weighed. The former are called "knots" and the latter "accepts." The combined weight of these two was subtracted from the original weight to determine the weight of fibers that passed through the 0.36 mm screen. These fibers were referred to as "fines."

Example 1

This example illustrates a representative method for making caustic treated pulp and cross-linking it.

A sample of Rayfloc®-J-LD (never dried) was obtained as a 33.7% solid wet lap from a Rayonier mill at Jesup, Ga., and is an untreated southern pine Kraft pulp sold by Rayonier Performance Fibers Division, Jesup, Ga. and Fernandina Beach, Fla. for use in products requiring good absorbency, such as absorbent cores in diapers. A 70.0 g (dry weight basis) sample was treated with an aqueous solution of 16% (w/w) sodium hydroxide at a consistency of 3.5%. Treatment was carried out at room temperature for about 10 min, and excess NaOH was then removed by suction filtration or centrifuge. The resulting caustic treated pulp was washed with excess water, neutralized to a pH of 5.4 with acetic acid solution (0.01 M) at a consistency of about 3.5%. The pulp then was formed into a sheet (12×12 inch) and treated while in the wet state with a 4.5% aqueous solution of glyoxylic acid by dipping and pressing to afford a sheet having 5% glyoxylic acid on fiber. The treated sheet was then dried and cured at 370° F. for about 15 min. The cured sheet was fiberized by feeding it through a Hammer Mill. The absorbent properties (free swell, absorbent capacity, absorbency under load, centrifuge retention) of the resulting fibers were then determined. Results obtained from sheets cross-linked in the same manner at different curing times are summarized in Table 1. Results summarized in Table 1 indicate that, longer curing time is preferred in the present invention to provide for complete cross-linking.

TABLE 1

Absorbent properties of fiber cross-linked with glyoxylic acid (5%) at different cure time: Cure temperature 370° F.

| Curing Time (min) | Absorbency Under Load (g/g) | Absorbent Capacity (g/g) | Free Swell (g/g) | Centrifuge Retention (g/g) |
|---|---|---|---|---|
| 15 | 9.0 | 10.6 | 21.0 | 0.37 |
| 10 | 8.9 | 10.0 | 20.0 | 0.46 |
| 5 | 10.0 | 11.1 | 25.0 | 0.60 |

Example 2

This example illustrates the effect of curing time on absorbent properties of a representative cross-linked fiber formed in accordance with the present invention.

Fibers were caustic treated and cross-linked with glyoxylic acid as in example 1 above, except that the caustic treated sheet was dried in an oven at 60° C. before treatment with glyoxylic acid (2.6%) solution. Final percentage of glyoxylic acid on fiber was 3% by weight, based on dry sheet weight. The results are shown in Table 2 below.

TABLE 2

Absorbent properties of fiber cross-linked with glyoxylic acid (3%) at various curing time: Cure temperature 370° F.

| Cure time (min) | Absorbency under Load (g/g) | Absorbent capacity (g/g) | Free Swell (g/g) | Centrifuge Retention (g/g) |
|---|---|---|---|---|
| —[1] | | | 10.0 | 0.97 |
| 2[2] | 8.6 | 10.2 | 21.5 | 0.72 |
| 3 | 8.5 | 9.9 | 22.0 | 0.51 |
| 5 | 8.4 | 9.9 | 22.4 | 0.51 |
| 10 | 8.5 | 10.1 | 22.0 | 0.50 |

[1]Mercerized pulp untreated with cross-linking agent glyoxylic acid.
[2]No curing was carried out on this sheet, only drying.

The results summarized in Table 2 reveal that the absorbent properties of the cross-linked fibers depend on curing time. Increasing the cure time generally results in a cross-linked fiber having better absorbent properties. In addition, the results in Table 2 reveal that partial curing may occur at low temperature, since centrifuge retention of caustic treated pulp decreased from 1.0 g to 0.72 g upon treatment with glyoxylic acid and drying at 60° C.

Example 3

This example illustrates the effect of increasing the amount of glyoxylic acid on absorbent properties of a representative cross-linked fiber formed in accordance with the present invention.

The pulp used in this example was Porosanier-J, which is commercially available from the Rayonier mill at Jesup, Ga., and was obtained in roll form. Five sheets (12×12 inch), each weighing about 70.0 g (dry weight base) were obtained from the roll. The sheets were treated with an aqueous solution of glyoxylic acid at room temperature and at various concentrations, and cured at 370° F. for 15 min. The results are shown in Table 3 below.

TABLE 3

Absorbent properties of fiber cross-linked with various amount of glyoxylic acid: Cure temperature 370° F. for 15 min (includes drying)

| % of glyoxylic acid on fiber | Absorbency under Load (0.3 psi) (g/g) | Absorbent Capacity (g/g) | Free Swell (g/g) | Centrifuge Retention (g/g) |
|---|---|---|---|---|
| 8.0 | 8.6 | 10.1 | 19.4 | 0.39 |
| 5.4 | 9.0 | 10.6 | 21.0 | 0.37 |
| 4.0 | 9.3 | 10.5 | 22.7 | 0.39 |
| 3.0 | 8.6 | 10.2 | 21.0 | 0.43 |
| 2.0 | 8.3 | 9.80 | 20.8 | 0.46 |

The results summarized in Table 3 reveal that the highest absorbency under load and free swell were achieved with about 4% cross-linking agent on fiber. Also, the results show that increasing the amount of cross-linking agent decreases the centrifuge retention capacity of the fiber. However, increasing the amount of cross-linking agent on fiber to about 8% did not show any substantial effect on fiber absorbent properties.

Example 4

This example illustrates the effect of curing temperature on absorbent properties of a representative cross-linked fiber formed in accordance with the present invention.

The pulp used in this example was Porosanier-J, commercially available from the Rayonier mill at Jesup, Ga., and obtained in the roll form. Five sheets (12×12 inch), each weighing about 70.0 g (dry weight base) were obtained from the roll. The sheets were treated with an aqueous solution of glyoxylic acid at about room temperature to provide a final percentage of glyoxylic acid on fiber of about 4% by weight, based on the sheet weight. The treated sheets then were cured at various cure temperatures for 15 min. Absorbent properties of cross-linked sheets as a function of cure temperature are evaluated and results are summarized in Table 4.

TABLE 4

Absorbent properties of fiber cross-linked with glyoxylic acid at various curing temperatures: Cure time 15 min

| Curing temperature ° F. | Absorbency under Load (g/g) | Absorbent capacity (g/g) | Free Swell (g/g) | Centrifuge Retention (g/g) |
|---|---|---|---|---|
| 300 | 8.5 | 9.6 | 20.3 | 0.62 |
| 320 | 8.4 | 9.7 | 21.5 | 0.52 |
| 340 | 9.0 | 10.4 | 21.8 | 0.50 |
| 370 | 9.3 | 10.5 | 22.7 | 0.39 |
| 420 | 9.2 | 10.3 | 22.3 | 0.39 |

The results summarized in Table 4 reveal that absorbency under load, absorbent capacity, and free swell increase with increasing cure temperature, whereas centrifuge retention capacity decreases with increasing cure temperature. These results indicate that cross-linking efficiency increases with increasing the cure temperature. However, increasing the cure temperature from 370 to 420° F. did not provide any substantial change in fiber absorbent properties.

Example 5

This example illustrates a representative method for making cross-linked fiber in the fluff from.

A sample of Rayfloc®-J-LD (never dried) was obtained as a 33.7% solid wet lap from Rayonier mill at Jesup, Ga. A 70.0 g (dry weight base) sample was treated with an aqueous solution of 4% (w/w) sodium hydroxide at a consistency of 3.5%. Treatment was carried out at room temperature for about 15 min, and excess NaOH was removed by suction filtration or centrifuge. The resulting caustic treated pulp was washed with excess water, neutralized to a pH of 5.4 with acetic acid solution (0.01 M) at a consistency of about 3.5%. The pulp was then treated while in the wet state with a 2.2% aqueous solution of glyoxylic acid by dipping and pressing to afford a fiber having 4% by weight glyoxylic acid. The treated fiber was then dried at room temperature, defiberized by feeding it through a hammermill (Kamas Mill H01, Kamas Industries AB, Vellinge, Sweden), and cured at 370° F. Fiber absorbent properties and bulk were then evaluated. Results obtained from fiber treated with various concentrations of sodium hydroxide and cross-linked in the same manner are summarized in Tables 5 and 6.

TABLE 5

Cross-linking of non mercerized and mercerized Rayfloc-I in the fluff form at constant curing temperature (370° F.).

| % of aqueous NaOH | Curing time (min) | Absorbency under Load (g/g) | Absorbent capacity (g/g) | Free Swell (g/g) | Centrifuge Retention (g/g) |
| --- | --- | --- | --- | --- | --- |
| — | 5 | 13.8 | 15.8 | 25.0 | 0.55 |
| — | 10 | 14.0 | 15.8 | 29.0 | 0.51 |
| 4 | 5 | 12.7 | 14.5 | 25.0 | 0.56 |
| 4 | 10 | 13.6 | 16.0 | 27.5 | 0.55 |
| 8 | 5 | 11.7 | 13.3 | 25.4 | 0.53 |
| 8 | 10 | 12.2 | 14.0 | 29.0 | 0.48 |

TABLE 6

Cross-linked fiber in fluff form, dry and wet bulk: cure temperature 370° F., cure time 10 min

| % of aqueous NaOH | Curing time (min) | Dry Bulk cc/g | Wet Bulk cc/g |
| --- | --- | --- | --- |
| — | 10 | 19.6 | 16.0 |
| 4 | 10 | 22.0 | 16.1 |
| 8 | 10 | 20.2 | 15.7 |

Example 6

This representative example illustrates the effect of using a mixture of cross-linking agents on the absorbent properties of cross-linked fibers.

The pulp used in this example was Porosanier-J, commercially available from the Rayonier mill at Jesup, Ga., and obtained in the roll form. Four sheets (12×12 inch), each weighing about 70.0 g (dry weight basis) were obtained from the roll. The sheets were treated at about room temperature with an aqueous solution of a mixture of glyoxylic acid and various polyepoxide cross-linking agents at various concentrations in the presence of an emulsifying agent Triton X-100 (0.1% of the total weight of cross-linking agents). The treated fibers were cured at 370° F. for 15 min. The absorbent properties of cross-linked fibers were evaluated and the results are summarized in Table 7 below.

TABLE 7

Absorbent properties of fiber cross-linked with a mixture cross-linking agents: Cure temperature 370° F. (includes drying and curing)

| Cross-linking agent) and % on Fiber | Absorbency under Load (0.3 psi) g/g | Absorbent capacity g/g | Free Swell g/g | Centrifuge Retention g/g |
| --- | --- | --- | --- | --- |
| Glyoxylic acid (3%) + PPGDGE (2%) | 8.4 | 10.2 | 21.6 | 0.46 |
| Glyoxylic acid (4%) + PPGDGE (1%) | 8.4 | 10.0 | 20.0 | 0.48 |
| Glyoxylic acid (3%) + DG-1,2-CHDC (2%) | 8.1 | 10.3 | 23.0 | 0.46 |
| Glyoxylic acid (4%) + DG-1,2-CHDC (1%) | 7.8 | 9.7 | 21.5 | 0.42 |

Example 7

This example reveals the percent of fines and knots in representative cross-linked fibers made in accordance with the present invention, when compared to commercially available cross-linked fibers.

TABLE 8

Fines and knots contents

| Fiber | Cross-linking agent | % of Cross-linking agent on fiber | % of fines | % of knots |
| --- | --- | --- | --- | --- |
| Porosanier | | | 2.1 | 12.4 |
| P & G (Pamper ® AL material) | | | 5.9 | 13.8 |
| HBA | | | 6.0 | 11.9 |
| Porosanier Fiber (sheet form) | Mixture of polymaleic acid (20%) and citric acid (80%) | 4.2 | 4.4 | 1.5 |
| Cross-linked fiber (sheet form) | Glyoxylic acid | 3.0 | 5.3 | 2.4 |
| Cross-linked fiber (sheet form) | Glyoxylic acid | 4.0 | 4.3 | 4.9 |
| Individualized cross-linked[1] fiber | Glyoxylic acid | 5 | 5.3 | 23.6 |
| Individualized cross-linked fiber[2] | Glyoxylic acid | 3 | 3.2 | 16.0 |
| Cross-linked fiber (sheet form) | Glyoxylic acid (80%) and Diglycidyl 1,2-cyclohexane dicarboxylate (2%) | 5.0 | 0.9 | 5.0 |

[1]Prepared from pulp with conventional purity.
[2]Prepared from caustic (4%) treated fiber.

As indicated in Table 8, the percentage of knots in representative fibers cross-linked in sheet form using caustic treated pulp is significantly lower than that for commercially available cross-linked fiber and fiber cross-linked in fluff form in accordance with the present invention using pulp with conventional purity.

Example 8

This example describes the "aging" test method used to study the resistance of representative samples of cross-linked fiber made in accordance with present invention to revert to uncross-linked fiber. Such reversion was observed in traditional cross-linked fiber made from cross-linking fibers with alkane polycarboxylic acids, such as citric acid.

The aging test was carried out on two representative samples of cross-linked fibers made in accordance with the present invention, as described in Example 4 above. Each sample weighed about 2.000 g, the samples were airlaid to pads each having a diameter of about 60.4 mm. One pad served as a blank, and the other was aged by heating it in an oven with a controlled humidity of 80% to about 85% at 90° C. for 20 hr. After the setting time, the sample pad was allowed to equilibrate in a 50% humidity environment at room temperature for 24 hours. The two pads (sample and blank) then were compressed with a load of about 7.6 psi for 60 seconds, the weights were removed, and the pads were allowed to equilibrate for 1 minute. The thickness of the pads were measured and bulk was determined.

The absorbent properties of blank and sample were determined by the absorbency test method described above. The results are summarized in Table 9 below.

TABLE 9

Absorbent properties of aged fiber

| Cross-linked Fiber (3% glyoxylic acid) | Dry Bulk cc/g | Absorbency Under Load g/g | Absorbent capacity g/g | Centrifuge Retention g/g |
|---|---|---|---|---|
| Aged Sample | 14.1 | 8.3 | 9.4 | 0.41 |
| Blank | 14.0 | 8.6 | 10.2 | 0.43 |

The results summarized in Table 9 reveal that the bulk and centrifuge retention of cross-linked fiber remained unchanged after heating the fiber at elevated temperature for a long period of time. These results indicate that the cross-linkage in the fibers cross-linked in accordance with the present invention are stable.

Example 9

This example provides the acquisition times for cross-linked fibers made in accordance with the present invention compared to commercially available cross-linked fibers. The fibers made in accordance with the present invention were prepared in accordance with Example 4 above.

The acquisition time was determined by the SART test method. The SART test method evaluates the performance of the cross-linked fibers as an acquisition layer in absorbent article. The test measures the time required for a dose of saline to be absorbed completely into the absorbent article. The test is conducted on a sample of an absorbent article obtained from a commercially available diaper (Huggies, from Kimberly-Clark). The sample had a circular shape having a diameter of 60.0 mm, usually cut from the center of the diaper core, and weighed about 2.6 g (±0.2 g).

In this test, the acquisition layer of the sample was replaced with an airlaid pad made from the fiber of the present invention. The fiber pad weighed about 0.7 g and was compressed with a load of a 7.6 psi for about 60 seconds before it was used in the sample.

The sample was placed into the testing cell with the nonwoven side up. The testing cell consisted of a plastic base and a funnel cup (obtained from Portsmouth Tool and Die Corp., Portsmouth, Va., USA). The base was a plastic cylinder having an inside diameter of 60.0 mm that was used to hold the sample. The funnel cup was a plastic cylinder having a hole with a star shape, the outside diameter of which is 58 mm. The funnel cup was placed inside the plastic base on top of the sample, and a load of about 0.6 psi having a donut shape was placed on top of the funnel cup.

The cell and its contents were placed on a leveled surface and dosed with three successive insults, each being 9.0 ml of saline solution, (0.9% by weight), the time interval between doses being 20 min. The doses were added with a Master Flex Pump (Cole Parmer Instrument, Barrington, Ill., USA) to the funnel cup, and the time in seconds required for the saline solution of each dose to disappear from the funnel cup was recorded and expressed as an acquisition time, or strikethrough. The third insult strikethrough time is provided in Table 10 below.

TABLE 10

Liquid acquisition time for absorbent articles containing representative cross-linked fibers and commercial fibers.

| Fiber | Cross-linking Agent | % of Cross-linking agent | $3^{rd}$ Insult (sec) |
|---|---|---|---|
| Porosanier | | | 21.0 |
| P & G (Pamper ® AL material) | | | 8.9 |
| Porosanier (sheet form) | Mixture of polymaleic acid (20%) and citric acid (80%) | 4.2 | 14.0 |
| Cross-linked fiber (sheet form) | Glyoxylic acid | 3.0 | 8.6 |
| Individualized cross-linked[1] fiber | Glyoxylic acid | 5.0 | 6.6 |
| Individualized cross-linked fiber[2] | Glyoxylic acid | 3.0 | 6.1 |
| Cross-linked fiber (sheet form) | glyoxylic acid (80%) and Diglycidyl 1,2-cyclo-hexane dicarboxylate (20%) | 5.0 | 9.0 |

[1]Prepared from pulp with conventional purity.
[2]Prepared from caustic (4%) treated fiber.

As shown in Table 10, the third insult strikethrough times for representative fibers formed in accordance with the present invention was lower than for commercially available cross-linked fiber. The liquid acquisition times for representative fiber formed in accordance with the present invention in fluff from were significantly less than for commercially available cross-linked fiber.

Example 10

The fibers of Example 7 were tested for ISO Brightness in accordance with TAPPI test methods T272 and T525. The results are summarized in Table 11 below:

TABLE 11

ISO Brightness

| Fiber | Cross-linking agent | ISO Brightness |
|---|---|---|
| Porosanier | | 91.4 |
| P & G (Pamper ® AL material) | | 78.5 |
| Cross-linked fiber (sheet form) | Glyoxylic acid | 87.8 |
| Cross-linked fiber (sheet form) | Glyoxylic acid | 88.0 |
| Individualized cross-linked[1] fiber | Glyoxylic acid | 84.1 |

TABLE 11-continued

ISO Brightness

| Fiber | Cross-linking agent | ISO Brightness |
|---|---|---|
| Individualized cross-linked fiber[2] | Glyoxylic acid | 83.9 |
| Cross-linked fiber (sheet form) | Glyoxylic acid (80%) and Diglycidyl 1,2-cyclo-hexane dicarboxylate (2%) | 89.1 |

[1]Prepared from pulp with conventional purity.
[2]Prepared from caustic (4%) treated fiber.

The results of Table 11 reveal that cellulose fibers cross-linked in accordance with the present invention provide improved ISO brightness, when compared to conventional cross-linked fibers While the invention has been described with reference to particularly preferred embodiments and examples, those skilled in the art recognize that various modifications may be made to the invention without departing from the spirit and scope thereof.

What is claimed is:

1. A cross-linked cellulosic fiber having a centrifuge retention capacity of less than about 0.48 grams of a 0.9% by weight saline solution per gram of fiber, and a third acquisition insult time of less than 10 seconds.

2. The cross-linked fibers of claim 1, wherein the fibers have an absorption capacity of at least about 9.0 g saline/g fiber.

3. The cross-linked fibers of claim 1, wherein the fibers have a dry bulk of at least about 12 cm$^3$/g fiber.

4. The cross-linked fibers of claim 1, wherein the fibers have a centrifuge retention of not more than 0.45 g saline/g fiber.

5. The cross-linked fibers of claim 1, wherein the fibers have a free swell of at least about 10.0 g saline/g fiber.

6. The cross-linked fiber of claim 1, wherein the fibers have knots and knits contents of less than about 5%.

7. The cross-linked cellulosic fibers of claim 1, wherein the cellulose fiber is a wood pulp fiber selected from the group consisting of hardwood pulp, softwood cellulose pulp obtained from a Kraft or sulfite chemical process, and combinations or mixtures thereof.

8. The cross-linked cellulosic fibers of claim 7, wherein the hardwood cellulose pulp is selected from the group consisting of gum, maple, oak, eucalyptus, poplar, beech, aspen, and combinations and mixtures thereof.

9. The cross-linked cellulosic fiber of claim 7, wherein the soft cellulose pulp is selected from the group consisting of Southern pine, White pine, Caribbean pine, Western hemlock, spruce, Douglas fir, and mixtures and combinations thereof.

10. The cross-linked cellulosic fibers of claim 1, wherein the cellulosic fiber is derived from one or more component selected from the group consisting of cotton linters, bagasse, kemp, flax, grass, and combinations and mixtures thereof.

11. The cross-linked fiber of claim 1, wherein the fibers have an ISO Brightness of greater than 80%.

12. A cross-linked cellulosic fiber prepared by contacting a cellulosic fiber with one or more cross-linking agents, whereby the fiber has a centrifuge retention capacity of less than about 0.48 grams of a 0.9% by weight saline solution per gram of fiber, and a third acquisition insult time of less than 10 seconds.

13. A cross-linked cellulosic fiber cross-linked by a cross-linking agent selected from one or more acid aldehyde organic molecules containing aldehyde and carboxylic acid functional groups, whereby the fiber has a centrifuge retention capacity of less than about 0.60 grams of a 0.9% by weight saline solution per gram of fiber, and a third acquisition insult time of less than 10 seconds.

14. The cross-linked cellulosic fiber of claim 13, wherein the acid aldehyde cross-linking agent is selected from the group consisting of glyoxylic acid, succinic semialdehyde, and mixtures and combinations thereof.

15. The cross-linked cellulosic fiber of claim 14, wherein a mixture of cross-linking agents is used, the mixture of cross-linking agents comprising a primary cross-linking agent and at least one secondary cross-linking agent.

16. The cross-linked cellulosic fiber of claim 15, wherein the primary cross-linking agent is selected from the group consisting of glyoxylic acid, succinic semialdehyde, and mixtures and combinations thereof.

17. The cross-linked cellulosic fiber of claim 15, wherein the secondary cross-linking agent is at least one polyepoxide having a substituent selected from the group consisting of hydrogen; hydrophobic saturated, unsaturated, cyclic saturated, cyclic unsaturated, branched, unbranched alkyl groups; and mixtures and combinations thereof.

18. The cross-linked celtulosic fiber of claim 17, wherein the polyepoxide is selected from the group consisting of 1,4 cyclohoxanedimethanol diglycidyl ether, diglycidyl 1,2-cyclohexanedicrboxylate, N,N-diglycidylaniline, N,N-diglcidyl-4-glycidyloxyaniline, diglycidyl 1,2,3,4-tetrahydrophthalate, glyccrol propoxylate triglycidyl ether, and mixtures and combinations thereof.

19. The cross-linked cellulosic fiber of claim 15, wherein the secondary cross-linking agent is one or more $C_2$–$C_9$ polycarboxylic acids selected from the group consisting of butantetracarbocylic acid, citric acid, itaconic acid, maleic acid, tartaric acid, and glutaric acid.

20. The cross-linked cellulosic fiber of claim 15, wherein the secondary cross-linking agent is one or more polycarboxylic acids selected from the group consisting of polyacrylic acid, polymaleic acid, polyitaconic acid, polyaspartic acid, and polymethacrylic acid.

21. The cross-linked cellulosic fiber of claim 13, wherein the fibers have an absorption capacity of at least about 9.0 g saline/g fiber.

22. The cross-linked fibers of claim 13, wherein the fibers have a dry bulk of at least about 12 cm$^3$/g fiber.

23. The cross-linked fibers of claim 13, wherein the fibers have a centrifuge retention of not more than 0.5 g saline/g fiber.

24. The cross-linked fibers of claim 13, wherein the fibers have a free swell of at least about 10.0 g saline/g fiber.

25. The cross-linked fiber of claim 13, wherein the fibers have knots and knits contents of less than about 5%.

26. The cross-linked cellulosic fiber of claim 13, wherein the cellulose fiber is a wood pulp fiber selected from the group consisting of hardwood pulp, softwood cellulose pulp obtained from a Kraft or sulfite chemical process, and combinations or mixtures thereof.

27. The cross-linked cellulosic fiber of claim 26, wherein the hardwood cellulose pulp is selected from the group consisting of gum, maple, oak, eucalyptus, poplar, beech, aspen, and combinations and mixtures thereof.

28. The cross-linked cellulosic fiber of claim 26, wherein the soft cellulose pulp is selected from the group consisting of Southern pine, White pine, Caribbean pine, Western hemlock, spruce, Douglas fir, and mixtures and combinations thereof.

29. The cross-linked cellulosic fiber of claim 13, wherein the cellulosic fiber is derived from one or more component selected from the group consisting of cotton linters, bagasse, kemp, flax, grass, and combinations and mixtures thereof.

30. The cross-linked cellulosic fiber of claim 15, wherein the mixture of cross-linking agents is a mixture selected from the group consisting of: a mixture of glyoxylic acid and citric acid; a mixture of glyoxylic acid and polymaleic acid; and a mixture of glyoxylic acid, citric acid, and polymaleic acid.

31. The cross-linked cellulosic fiber of claim 15, wherein the mixture of cross-linking agents is a mixture selected from the group consisting of: a mixture of glyoxylic acid and citric acid; a mixture of glyoxylic acid and a terpolymer of maleic acid, vinyl acetate, and ethyl acrylate; and a mixture of glyoxylic acid, citric acid, and a terpolymer of maleic acid, vinyl acetate, and ethyl acrylate.

* * * * *